United States Patent
Allan et al.

(10) Patent No.: US 10,004,884 B2
(45) Date of Patent: Jun. 26, 2018

(54) NEGATIVE PRESSURE WOUND TREATMENT SYSTEM

(71) Applicants: University of Washington, Seattle, WA (US); Board of Regents, The University of Texas System, Austin, TX (US)

(72) Inventors: Christopher H. Allan, Seattle, WA (US); Muthu B. J. Wijesundara, Fort Worth, TX (US)

(73) Assignee: University of Washington, Seattle, WA (US)

( * ) Notice: Subject to any disclaimer, the term of this patent is extended or adjusted under 35 U.S.C. 154(b) by 525 days.

(21) Appl. No.: 14/661,809

(22) Filed: Mar. 18, 2015

(65) Prior Publication Data

US 2015/0343188 A1    Dec. 3, 2015

Related U.S. Application Data

(60) Provisional application No. 61/955,539, filed on Mar. 19, 2014.

(51) Int. Cl.
| | |
|---|---|
| *A61M 1/00* | (2006.01) |
| *A61M 35/00* | (2006.01) |
| *A61F 13/00* | (2006.01) |
| *A61F 13/10* | (2006.01) |

(52) U.S. Cl.
CPC ....... *A61M 35/00* (2013.01); *A61F 13/00068* (2013.01); *A61F 13/104* (2013.01); *A61M 1/0088* (2013.01); *A61M 1/0023* (2013.01); *A61M 1/0084* (2013.01); *A61M 2205/3303* (2013.01); *A61M 2205/3584* (2013.01)

(58) Field of Classification Search
CPC .............. A61M 1/0088; A61M 1/0084; A61M 1/0058; A61M 35/00; A61M 1/0023; A61M 2205/3303; A61M 2205/3584; A61F 13/00068; A61F 13/104

See application file for complete search history.

(56) References Cited

U.S. PATENT DOCUMENTS

| | | | |
|---|---|---|---|
| 4,706,658 | A | 11/1987 | Cronin |
| 5,328,449 | A | 7/1994 | Andrews et al. |
| 6,406,447 | B1 * | 6/2002 | Thrash ............... A61C 17/0211 601/159 |
| 7,279,612 | B1 | 10/2007 | Heaton et al. |
| 8,100,887 | B2 | 1/2012 | Weston et al. |

(Continued)

FOREIGN PATENT DOCUMENTS

| | | |
|---|---|---|
| EP | 1476106 B1 | 4/2009 |
| WO | WO2009125383 A1 | 10/2009 |

*Primary Examiner* — Ariana Zimbouski
(74) *Attorney, Agent, or Firm* — Perkins Coie LLP

(57) ABSTRACT

A protective and permissive healing medical device comprising a sealable enclosure made from a flexible and see-though dressing, coupled with a scaffold structure capable of separating portions of the inner surface of the sealable enclosure from the outer portions of an extremity sealed inside the device, a plurality of ports for delivering materials into and extracting mediums from the sealable enclosure consistent with a therapeutic environment for the injury within the device, and a plurality of digit receiving portions facilitating individually articulable movement during healing within the sealable enclosure.

20 Claims, 9 Drawing Sheets

(56) References Cited

U.S. PATENT DOCUMENTS

| | | |
|---|---|---|
| 8,350,115 B2 | 1/2013 | Heaton et al. |
| 8,444,622 B2 | 5/2013 | Eckhoff et al. |
| 2002/0060221 A1* | 5/2002 | Grinberg ............ A41D 19/0072 221/27 |
| 2005/0191372 A1* | 9/2005 | Stenzler ................ A61L 2/0094 424/718 |
| 2006/0116620 A1* | 6/2006 | Oyaski ................ A61M 1/0084 602/41 |
| 2006/0155260 A1* | 7/2006 | Blott .................... A61M 1/0001 604/543 |
| 2008/0215019 A1* | 9/2008 | Malamutmann .... A61M 1/0058 604/305 |
| 2013/0072829 A1 | 3/2013 | Fausti et al. |
| 2013/0204210 A1* | 8/2013 | Pratt .................... A61M 1/0031 604/290 |
| 2014/0005616 A1* | 1/2014 | Moreland ............... A61L 15/44 604/292 |
| 2014/0288621 A1* | 9/2014 | Efremkin ............. A61N 5/0624 607/89 |

\* cited by examiner

NEGATIVE PRESSURE WOUND TREATMENT SYSTEM

CROSS-REFERENCES TO RELATED APPLICATIONS

This application claims the benefit, under 35 U.S.C § 119(e), of U.S. provisional patent application No. 61/955,539 filed Mar. 19, 2014, entitled "Bioengineered Smart-Glove for Regenerative Healing of Extremity Trauma (RE-HEAL GLOVE)," which is hereby incorporated by reference in its entirety.

STATEMENT OF GOVERNMENT LICENSE RIGHTS

This invention was made with government support under grant number W911NF-12-1-0145 awarded by the U.S. Army Research Office (ARO). The government has certain rights in the invention.

BACKGROUND OF THE INVENTION

Extremities are extensively used parts of the body and highly susceptible to injury due to their exposed location and active involvement in tasks. Restoring functional and aesthetic characteristics after injury is difficult in such specialized anatomy, particularly of the hands and feet. Patients require protective and permissive healing environments in response to injury. Current treatment methods and devices are not protective environments, but instead are destructive environments. Current treatment methods and devices disrupt blood vessels surrounding the injury or disrupt healing during dressing changes, preclude effective assessment of treatment without causing additional pain or injury, or result in massive scarring. Accordingly, there is a need for improved systems and methods for treatment of wounds on extremities.

SUMMARY OF THE INVENTION

Devices and systems to enable regenerative healing of injuries in a permissive and protective environment are described. Embodiments of the present invention relate to technologies that promote faster and undisrupted healing, and support localized treatment regimens. Embodiments of the present invention further support healing injuries in regions of the body with particularized anatomy and difficult contours, such as extremities like hands and feet and digits like fingers and toes. More specifically, embodiments of the present invention relate to devices and systems for supporting tailored treatments to injuries in the extremities, such as the hands and feet, or digits, such as fingers and toes, of a patient. Though the following disclosure discusses in particular embodiments of the invention treating an extremity or a digit of an extremity, one having skill in the art will see applications of the present invention to injuries of other regions of the body.

Merely by way of example of an embodiment for treating an injury to the hand, the invention is applied via a device for healing an injury on a hand by placing the hand within a sealable enclosure made from a flexible and at least partially translucent material combined with a scaffold system within the sealable enclosure to separate at least portions of the inner surface of the sealable enclosure from the outer surface of the hand, and also a plurality of ports coupled to the sealable enclosure for maintaining a therapeutic environment within the sealable enclosure. The partially translucent material of the sealable enclosure is configured to seal and create a fluid tight environment at least around the injury. The sealable enclosure includes digit receiving portions for the fingers of the enclosed hand. Each digit receiving portion is individually articulable and may move independently relative to the other digit receiving portions.

The flexible material of the sealable enclosure permits motion of the enclosed injury, extremity, or digits, thereby expediting healing and permitting additional therapy earlier than conventional devices. Without motion during healing, an injured extremity is susceptible to massive scarring due to the layers of tissue and systems such as bone, cartilage, ligaments, tendons, skin, nerve and attendant vessels scarring in non-functional masses. These layers of tissue heal in response to the loads placed on them during healing. Current treatment methods and devices immobilize the extremity to a greater or lesser extent, leaving behind proteins that facilitate scar formation and scar growth. Devices that heal the injury in a static position create conditions conducive to permanent static positions of the extremity or limited mobility. Current devices employing negative pressure therapy utilize rigid inserts to assist creating uniform pressure throughout an enclosure, such that the limited mobility within the rigid insert becomes immobile when combined with the negative pressure.

In accordance with some embodiments, the flexible material permits a full range of motion of the extremity or digits enclosed within the device. In some embodiments, the motion of individual digits within the sealable enclosure is independent of motion of the other digits, such that the motion of each digit within the device is individually articulable relative to the other digits' motion. The flexible material of alternative embodiments permits motion greater than immobility when subject to a negative pressure environment. Embodiments of the invention permit natural motion of the extremity and digits, and as a result, the collagen and other fibers that otherwise align in directions creating scar tissue instead either do not form, or if they do form are reabsorbed, and fibers aligned with the extremity's motion are strengthened. Such motion enabled by embodiments of the invention properly rebuild and nourish tissue during healing. The need for external fixtures to create proper postural alignment is reduced or eliminated by a flexible enclosure of embodiments of the present invention.

An at least partially translucent material of the sealable enclosure permits visual assessment of the injury, and injury response to given treatment, without physically removing the enclosure. As a result, embodiments of the invention may be kept on the injury for longer durations than current treatment devices. Currently available devices must be changed frequently, as often as every forty-eight hours per the instructions of some contemporary devices, to assess the injury and avoid potential bacteria and infection buildup and growth; each change disrupts healing. By comparison, embodiments of the present invention may remain on the injury without removal for periods in excess of one week, thereby reducing disrupted healing. Patient pain is therefore reduced as well, especially as compared to currently available devices and dressings in which the dressing has adhered to the injury. Dressing changes can be painful processes inducing bleeding and stunting any healing that may have been occurring. Embodiments of the present invention avoid these painful and disruptive dressing changes. Particular benefits of leaving a healing device on for prolonged periods without disrupting the tissue during dressing changes are reduced infection rates and improved skin graft applications. In currently available devices, skin grafts are prone to separate from the target tissue during device or dressing changes, as the skin graft will adhere to the device or dressing and not just to the target tissue.

To further reduce disrupting healing during application and removal of the device, embodiments of the present invention may be formed from two main housing components: a flexible upper layer and a flexible lower layer sealed around peripheral seams of the two layers. The two layered system facilitates application and removal of the device without manipulating the extremity. Extremity manipulation during application or removal of contemporary devices induces patient pain as well as disrupts any regenerative healing occurring in the wound.

Embodiments of the invention can further be modular, creating the sealed and therapeutic environment for the injured area of an extremity or a digit only, and not enclosing or limiting the patient's otherwise healthy portions. For example, if only a single finger required treatment the device could be applied to the one finger only, rather than to the entire hand. Similarly if the fingertips of the digits were healthy then the device may be configured without fingertip portions and can include finger openings configured to form a seal around the base of each finger. The device can further be modified to be size appropriate, creating a sealed and therapeutic environment for the injured portion only; for illustration purposes only, if a fingertip were injured the device could be adapted for localized application to provide the healing environment to no more than that affected area. In one embodiment of the invention, three-dimensional (3D) imaging and scans of the extremity are taken. This imagery is provided to 3D fabrication software, creating a custom-sized sealable enclosure for healing devices for each patient.

Some conventional approaches for healing within an enclosed environment do not sufficiently separate contact between the injury and the device or system treating the injury. Particularly in negative pressure treatment regimens, blood vessels may grow in random directions. This random directional growth may result in blood vessels or other tissues healing onto or into the device or dressing in contact with the injury. This disrupts regenerative healing during treatment, and causes bleeding and patient pain when the device or dressing is removed. Further, skin grafts that are difficult to apply in contoured regions of extremities, such as inter-digit webspaces, are more prone to failed adhesion during dressing changes that contact and bind to the injury site. In embodiments of the present invention, a scaffold system placed between the sealable enclosure and the wound precludes such destructive contact and promotes faster and undisrupted healing. In one embodiment, the scaffold is a fixture coupled to the enclosure that physically props, or tensionally pulls, the enclosure away from the outer surface of the enclosed extremity. In some embodiments, the scaffold comprises a porous membrane and further facilitates treatment by creating a fluid flow cavity relative to the inner surface of the sealable enclosure to aid in delivery of materials to an injured area or removal of a medium from the enclosure.

In another embodiment, the scaffold itself is seeded with therapeutic agents. The presence of seeded scaffolds, for example seeded with donor tissue like skin grafts and bone grafts or infused stem cells, accelerates healing. Seeded scaffolds may also include osseointegrated tools, like pins and screws, coupled with residual bones. Seeded scaffolds as mentioned can further be custom created, molded and shaped for each patient through 3D imaging and fabrication.

The plurality of ports enable the various functions within the device according to various embodiments of the invention. In one embodiment, the plurality of ports create a negative pressure environment conducive for healing injuries within the sealable enclosure. The plurality of ports comprise one or more suction ports to create the negative pressure environment. Embodiments of the invention employing a scaffold system with a suction port system provide uniform negative pressure throughout the enclosure as the suction ports are not sealed by the extremity or other potential obstructions due to the separation the scaffold creates between the extremity and sealable enclosure. Current state of the art devices are prone to suction failures around the complex contours of extremities such as inter-digit webspaces or the ends of digits, the fluid flow cavity created by the scaffold in embodiments of the invention are not prone to such suction failures. The suction ports may further remove material from the injured site such as fluid and other exudates.

Other embodiments further include delivery ports to deliver materials into the sealable enclosure as well to mobilize healing and restorative aspects of the injured tissue. Materials delivered by the delivery ports comprise therapeutic materials such as antibiotics, growth factors, cytokines and cells. Materials delivered by the delivery ports in alternative embodiments comprise other materials such as electrical stimulants, water solutions, and air. Embodiments incorporating both suction ports and delivery ports enable wound irrigation, maintenance of a prescribed fluid environment for the injury, or a sustained aqueous environment. Still other embodiments place both a suction port and a delivery port within the same port by way of a two-way valve.

Other embodiments of the invention couple an array of sensors to the sealable enclosure. The sensors gather and monitor metrics within the device such as temperature, oxygen tension, pH levels, bacteria loads, and inflammatory responses. In other embodiments, the sensors further measure the properties of the suction ports or delivery ports to measure and coordinate metrics such as mass flow rate and time of suction or delivery. The sensor array is further integrated with interface devices in certain embodiments to display or record the sensor data. The sensor array in alternative embodiments is coupled to at least one control module to adjust a property within the sealable enclosure or of the plurality of ports in response to the conditions received by the sensor array. The control module adjustments include actuating the ports to apply a vacuum, irrigate a wound, creating an aqueous environment, or applying a certain material.

The protective environment of embodiments of the present invention permitting beneficial movement, longer injury protection durations due to less frequent dressing changes, delivery of materials promoting healing, and maintenance of a therapeutic environment around the injury as discussed previously controls inflammation and promotes the in situ expansion of progenitor cell populations. In embodiments of the invention that focus on the digits, this in situ expansion of progenitor cell populations is more pronounced as a fluid tight environment coupled with delivery of treatment enhances the progenitor cell population growth at the nail bed. Providing the aforementioned conditions improves healing and extremity restoration.

These and other embodiments of the invention along with many of its advantages and features are described in more detail in conjunction with the text below and attached figures.

BRIEF DESCRIPTION OF THE DRAWINGS

The foregoing aspects and many of the attendant advantages of this invention and its embodiments will become more readily apparent when the accompanying detailed description is taken in conjunction with the following figures.

DETAILED DESCRIPTION OF THE INVENTION

Figure 1A:
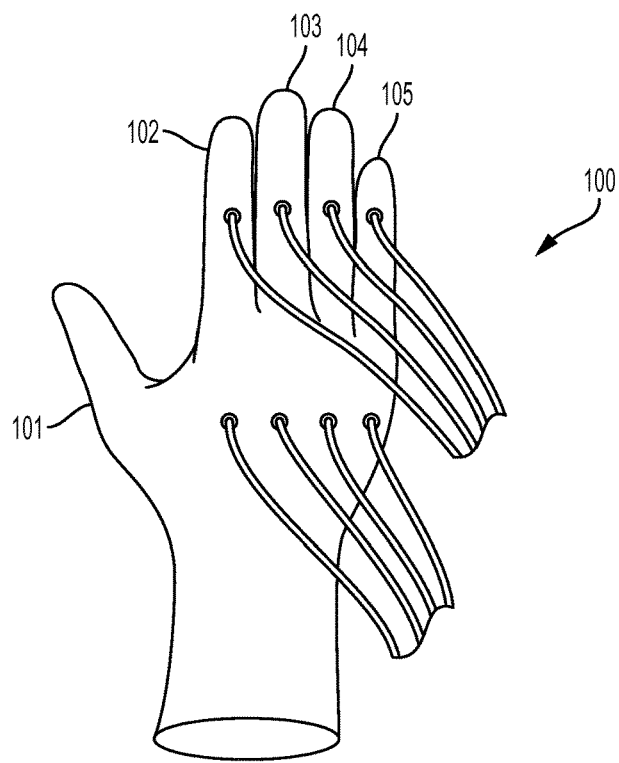
FIGS. 1A-1B illustrate a flexible enclosure in a first position and a flexed position with individually articulable locations of digits relative to other digits according to an embodiment of the present invention.

Embodiments of the present invention relate to technologies to heal an injury in a protected and permissive environment to promote faster and undisrupted healing, and support localized treatment regimens. Embodiments of the present invention further support healing injuries in regions of the body with particularized anatomy and difficult contours, such as extremities like hands and feet and digits like fingers and toes. Though the following detailed description and associated figures illustrate an embodiment of the invention treating an extremity or a digit of an extremity, one having skill in the art will see applications of the present invention to injuries of other regions of the body.

An embodiment of the invention is applied by a medical device having a sealable enclosure made from a flexible material that is at least partially translucent. When sealed around an extremity or digit, or around an injury to an extremity or digit, the sealable enclosure creates a fluid tight enclosure for the injury. The flexible material of the sealable enclosure enables ranges of motion of the extremity enclosed by the sealable enclosure that promote proper alignment of collagen fibers that grow incident to the healing process of the injury. In other embodiments, a scaffold structure is coupled to the sealable enclosure to separate contact between the inner surface of the flexible material of the medical device and at least a portion of the outer surface of an enclosed extremity. The contact separation precludes adhesion of the injury or any healing mediums such as blood clots, blood vessels, skin grafts and the like from adhering to the surface of the sealable enclosure. A plurality of individually addressable ports connected to the sealable enclosure controls the environment within the sealable enclosure. The enclosure itself has at least one individually articulable digit receiving portion, and motion of the digit receiving portion is independent of other digit receiving portions present, if any, to promote proper collagen fiber alignment of the healing tissue of the injury.

In one embodiment, the sealable enclosure of the device encloses at least a portion of an extremity. Certain embodiments of the invention are modular and do not enclose uninjured extremity portions or extremity portions that do not require enclosure as part of treatment; for example in one embodiment of the invention treating a hand, the thumb is healthy and the sealable enclosure does not enclose this healthy digit. The sealable enclosure encloses a sufficient portion of an extremity such that a fluid tight environment encompasses an injury to the extremity or digit.

The sealable enclosure in accordance with some embodiments comprises two complementary layers, each layer having a peripheral sealing interface such that when at least a portion of each respective sealing interface aligns with the other sealing interface they integrate and form an enclosed cavity that may house a received extremity or digit. The sealing interfaces may be glue or other adhesives, magnetic pairings, or an interlocking groove on one layer and a locking ridge on the other layer such that joining the groove and ridge forms a seal similar to a Ziploc® function. One having skill in the art can envision other sealing interfaces. In some embodiments, at least a portion of the peripheral sealing interface comprises an anchor sealing interface for securing the layer of the sealable enclosure to an anchor; appropriate anchors include the patient's skin, or another sealable enclosure.

In an alternative embodiment, the sealable enclosure is a single housing structure with at least one receiving aperture. The rim of a receiving aperture comprises an anchor sealing interface. The single housing structure embodiment slips over an extremity or digit to sufficiently enclose an injury and the anchor sealing interface seals to an appropriate anchor to create a fluid tight environment within the single housing structure. Appropriate anchors may include the skin of the extremity or digit, or another sealable enclosure. For example, in one embodiment the patient wears a fingerless glove and the sealable enclosure is an attachable finger portion that seals onto the finger openings of the fingerless glove via the anchor sealing interface. The anchor sealing interface of the extremity receiving aperture may be glue or other adhesives, magnetic pairings, or a mechanical coupling, such as an interlocking groove on one layer and a locking ridge on the other layer such that joining the groove and ridge forms a seal similar to a zipper storage bag. In another example, for illustrative purposes only, the sealable enclosure is a finger portion only that slips over the target finger and the anchor sealing interface seals to the skin of the patient by way of an adhesive on the anchor sealing interface.

In still other embodiments, the peripheral sealing interface of the sealable enclosure, whether a two layer system or a single housing structure, has no anchor sealing interface and is sealed to an anchor by an external adhering tool such as tape or other adhesive film, staples, or other securing mechanism.

According to one embodiment, the sealable enclosure is flexible to permit motion of an extremity during healing. In some embodiments, the flexibility is such that an enclosed extremity enjoys a full range of natural motion to promote proper collagen fiber alignment of healing tissue and reduce scarring. In alternative embodiments, the flexibility is less than a full range of motion, but greater than immobility experienced when the sealable enclosure is subjected to a negative pressure environment as with current devices and techniques.

Embodiments of the invention have a sealable enclosure permitting visual inspection within the device; that is, the sealable enclosure is at least partially translucent to permit visual assessment of an enclosed injury and healing response to treatment without removing the sealable enclosure. In some embodiments, the sealable enclosure is transparent. In alternative embodiments, the sealable enclosure is at least partially translucent at selective locations to permit visual assessment of an enclosed injury and healing response to treatment at certain locations of the sealable enclosure only.

In some embodiments, the material the sealable enclosure is built from comprises medical grade silicone. In an alternative embodiment, the material the sealable enclosure is built from is silicone rubber. In another embodiment, the material the sealable enclosure is built from is polyurethane. In another embodiment, the material the sealable enclosure is built from is polyethylene. In yet another embodiment, the material the sealable enclosure is built from is urethane rubber. One having skill in the art can envision combinations of these materials or other suitable materials consistent with the properties of the listed materials and disclosures of this description.

According to certain embodiments, a scaffold structure prevents contact between the injury and the inner surface of the sealable enclosure. In one embodiment, the scaffold is a fixture coupled to the sealable enclosure. In one embodiment, the fixture is coupled to the inner surface of the sealable enclosure such that it props the inner surface of the sealable enclosure away from the outer surface of the extremity. Embodiments of the invention with such a propping fixture coupled to the inner surface of the sealable enclosure have at least one propping fixture located relative to the injury such that the sealable enclosure does not contact the injury while the extremity is static or in motion. In one embodiment, the propping fixture is a hoop or ring lining the inner surface of the sealable enclosure. In another embodiment the propping fixture is a support member projecting inward from the inner surface of the sealable enclosure. In some embodiments, a propping fixture comprises the same material as the sealable enclosure, but in alternative embodiments is at least as dense as the sealable enclosure material.

In another embodiment, the fixture is coupled to the outer surface of the sealable enclosure. This outer surface fixture has a tensile modulus at least greater than that of the sealable enclosure such that it pulls the sealable enclosure away from the outer surface of an enclosed extremity. The higher rigidity of the outer surface fixture precludes the sealable enclosure from collapsing inward towards the outer surface of the extremity while static or in motion.

In both the propping fixture embodiment and pulling fixture embodiment the separation between the inner surface of the sealable enclosure and the outer surface of the enclosed extremity creates a fluid flow cavity layer. The fluid flow cavity layer between the inner surface of the sealable enclosure and outer layer of the enclosed extremity creates a space for fluid or other material delivered into the sealable enclosure to traverse the interior of the sealable enclosure without blockage or flow impedance otherwise. The fluid flow cavity layer also prevents suction seal of the outer surface of the extremity, exudate, or other material against a suction port coupled to the sealable enclosure. In other embodiments, the separation between the inner surface of the sealable enclosure and the outer surface of the extremity creates a fluid interface cavity layer. The fluid interface cavity layer maintains contact between an injury and prescribed materials and fluids delivered to the injury site.

In some embodiments, the scaffold structure comprises a membrane coupled to the inner surface of the sealable enclosure. The membrane may be porous with pore diameters of, for example, less than 750 microns, less than 500 microns, or less than 250 microns. In some embodiments, the porosity of the membrane is, for example, greater than fifty percent (50%). The membrane may comprise, for example, medical grade silicone, or may comprise some other flexible and hydrophobic materials such as silicone composites and polyethylene.

In another embodiment, the membrane coupled to the inner surface of the sealable enclosure is separated from directly contacting the inner surface of the sealable enclosure by pillars or support members situated between the inner surface and the membrane. Pillars perform functions similar to support members as previously disclosed in relation to structures to separate a sealable enclosure from an enclosed extremity. The separation of the membrane and the inner surface creates a fluid flow cavity layer. The fluid flow cavity layer creates a space for fluid or other material delivered into the sealable enclosure to traverse the interior of the sealable enclosure without blockage or flow impedance otherwise. The fluid flow cavity layer also prevents suction seal of the outer surface of the extremity, the membrane, exudate, or other material against a suction port coupled to the sealable enclosure.

In another embodiment, the membrane is coupled with extremity fixtures. When an extremity is enclosed in an embodiment of the invention with a membrane coupled with extremity fixtures, at least a portion of the membrane and an outer surface of the extremity are separated and do not contact the other. The description for extremity fixtures coupled to the membrane are similar to the propping and pulling fixtures as described for a scaffold coupled to the sealable enclosure discussed previously. The separation between the membrane and the outer surface of the extremity creates a fluid interface cavity layer. The fluid interface cavity layer maintains contact between an injury and prescribed materials and fluids delivered to the injury site.

In another embodiment, the membrane further comprises therapeutic agents coupled to the membrane. Coupling in one embodiment is by infusing a therapeutic agent such as collagen, stem cells, grow factors and the like into the membrane for release into the injury. Coupling in another embodiment attaches skin grafts or tissue grafts to the membrane for application and transfer to the injury. Coupling in yet another embodiment integrates tools and structures such as pins, screws, and 3D fabricated parts for the membrane to hold in place while the injury heals around and osseointegrates the tool or structure into the injury. In other embodiments, the membrane is the tool or structure itself, particularly molded or constructed to both separate contact between the injury and the inner surface of the sealable enclosure and deliver a therapeutic agent to the injury or provide tool or structure support to the injury. The therapeutic agents disclosed here (collagen, stem cells, growth factors, skin grafts, tissue grafts, tools, structures, 3D fabricated parts) are not exhaustive and one having skill in the art can envision other therapeutic agents suitable for coupling to a membrane to facilitate healing of an injury.

Other embodiments of the invention comprise a plurality of ports for controlling the therapeutic environment within the sealable enclosure. In one embodiment, the plurality of ports comprises at least one suction port to extract at least one medium from within the sealable enclosure. In embodiments creating negative pressure environments, the medium extracted is air or other gases within the sealable enclosure. Other embodiments extract mediums such as injury exudate, and other fluids. In another embodiment, the plurality of ports comprises at least one delivery port for delivering a material to the outer surface of the extremity. Materials delivered by a delivery port include antibiotics, other pharmaceuticals, growth factors, cytokines, stem cells, fluid solutions, and air. In some embodiments, the plurality of ports comprises at least one suction port and at least one delivery port. In embodiments with both suction ports and delivery ports, the delivery of fluids and suction of fluids by way of the respective ports enables injury irrigation within the sealable enclosure or maintenance of an aqueous environment otherwise. In another illustrative example of embodiments with both suction and delivery ports, the balance of delivery of air or other gas by a delivery port and suction of the air or other gas by a suction port enables uniform pressure even in highly contoured areas of the extremity.

In some embodiments, the plurality of ports are individually addressable, such that the operation and function of one port is independent from the operation and function of another port. For example, in an illustrative embodiment, a control module coupled to the plurality of ports elects which port delivers materials and which port extracts a medium and the time each function occurs. Such a port system enables localized and customized therapy application. In one embodiment, a port that delivers material at one time may be elected for suction at a another time. Embodiments with multifunction valves are capable of both delivery and suction from a single port at the control module's command. Individual digits of an extremity can receive isolated treatment by embodiments with individually addressable ports.

The function to turn a port on or off may be achieved by mechanical clamps in some embodiments, and by electronic controls in other embodiments. In alternative embodiments, a single port within the plurality of ports serves more than one function by way of multifunction valve, such as a two-way valve to support both suction of mediums and delivery of materials. Individually addressable ports permit variable treatment regimens for different injuries within the same enclosure or address discrete locations of the same injury.

In one embodiment, a vacuum pump unit is coupled to the plurality of ports. The vacuum pump unit draws out at least one medium through at least one suction port. The vacuum pump unit may provide intermittent or selective suction, or may provide continuous suction. In some embodiments, the vacuum pump unit is coupled to a control module to direct the time and rate of suction and which port is activated for suction and extraction of the medium. In certain embodiments, the vacuum pump unit suction rate through the suction ports is relative to the delivery rate through the delivery ports. The adjustment of suction rate relative to the delivery rate enables maintenance of an aqueous environment within the sealable enclosure, build up of delivered materials within the device, or rapid extraction of delivered materials within the device.

In one embodiment, the vacuum pump unit is coupled to a reservoir storing a first material to be delivered to the sealable enclosure. In another embodiment, at least one pump is coupled to the reservoir to push material from the material reservoir to the sealable enclosure. In one embodiment the pump configured to push material is a syringe pump. In other embodiments the vacuum pump unit draws material from the material reservoir through the sealable enclosure. The first material may be transported to a delivery port through delivery lines and a first manifold system. In alternative embodiments, the reservoir and the delivery port are co-located. Other embodiments have a reservoir network of multiple reservoirs for additionally storing a second material, a third material, and so on as relevant for a treatment regimen. In some embodiments, a control module adjusts input properties of the delivered material. Input properties include which material to deliver from the reservoir network, temperature of the material, flow rate of the material, which delivery port delivers the material, time of delivery of the material and the like.

In another embodiment the vacuum pump unit couples the suction ports to a second manifold system for transporting the extracted medium from the sealable enclosure. In alternative embodiments the suction port is not coupled to a manifold system, and the suction port releases the extracted medium into an atmosphere external from the interior of the sealable enclosure. In some embodiments, an exudate reservoir is coupled to the second manifold system and collects the medium the suction ports extract from within the sealable enclosure. In certain embodiments, a control module couple to the suction ports dictates output properties of medium. Output properties include extraction flow rate, which suction port is activated, and time or frequency of extraction.

Certain embodiments of the invention comprise a plurality of digit receiving portions. Each digit receiving portion is individually articulable for movement. In some embodiments, each digit receiving portion moves independently from and with motion relative to the other digit receiving portions. In another embodiment, multiple digit receiving portions move dependent on the motion of other digit receiving portions.

In some embodiments, digit receiving portions are attached to an extremity housing portion. Attachment in one embodiment is by an anchor sealing interface as discussed previously. For an illustrative example of such an embodiment for injuries to the hand, the digit receiving portions comprises finger portions, and the extremity housing portion comprises a structure around the palm and back of the hand, much like a fingerless glove. The finger portions attach to the fingerless glove by anchor sealing interfaces as previously disclosed in this detailed description. In other embodiments, the digit receiving portions are extensions of the extremity housing portion for a seamless integration of the two components. In still other embodiments, the digit receiving portions enclose the respective digits only and do not attach to external enclosures such as an extremity housing portion.

In yet another embodiment, the digit receiving portions are coupled to other digit receiving portions.

In another embodiment, the digit receiving portions are sealable apertures coupled to an extremity housing portion. In such an embodiment, the digits of the extremity do not require enclosure within the device; the digit receiving portion is a variable length extension in the direction of the digit extending from the extremity housing portion. The digit receiving portion comprises an aperture at the end of each digit receiving portion with a sealable interface along the rim of the aperture configured to adhere to the skin of a received digit.

Other embodiments of the invention comprise a plurality of sensors to detect biological metrics or data of conditions within the sealable enclosure. Other embodiments of the invention also couple a plurality of sensors to the plurality of ports to measure the properties of the medium extracted from, or materials delivered to, the sealable enclosure. According to some embodiments of the invention having a plurality of sensors, a sensor interface is coupled to the plurality of sensors. The sensor interface records the information collected by the plurality of sensors in one embodiment. In another embodiment the sensor interfaces stores the information collected by the plurality of sensors, and in yet another embodiment the sensor interface displays the information collected by the plurality of sensors.

In some embodiments, the plurality of sensors are coupled to a control module and a plurality of ports. The control module receives information collected by the plurality of sensors and adjusts an input property of the delivered materials in response to the sensor information. The control module adjusts the input property by dictating the function of a corresponding delivery port. Input properties adjusted by the control module include which material to deliver, temperature of the material, flow rate of the material, which delivery port delivers the material, time of delivery of the material and the like. For example if the sensor detects bacteria build up in a digit receiving portion, the control module delivers antibiotics to the delivery port corresponding to that digit receiving portion. In another illustrative example, for treatment regimens prescribing negative pressure within the sealable enclosure, if the sensors detect a build up of pressure the control module increases the suction rate of the suction ports to reestablish a negative pressure environment.

In another embodiment, the control module receives information collected by the plurality of sensors and adjusts an output property of an extracted medium in response to the sensor information. The control module adjusts the output property by dictating the function of a corresponding suction port. Output properties adjusted by the control module include extraction flow rate, which suction port is activated, and time or frequency of extraction. One having skill in the art can envision other output properties, or input properties, the control module could adjust.

FIG. 1A illustrates an embodiment of a sealable enclosure 101 in a first position 100. The sealable enclosure 101 comprises a first individually articulable digit receiving portion 102, a second individually articulable digit receiving portion 103, a third individually articulable digit receiving portion 104, and a fourth individually articulable digit receiving portion 105. One having skill in the art can envision a different number of individually articulable digit receiving portions, for example in embodiments of enclosing a hand there may be five digit receiving portions (four fingers and a thumb). In another illustrative example of a modular embodiment (not shown) there may be fewer digit receiving portions than illustrated in FIG. 1A.

In one embodiment, each individually articulable digit receiving portion 102, 103, 104, and 105 is configured to move relative to sealable enclosure 101. Each individually articulable digit receiving portion is further configured to move independently relative to the other individually articulable digit receiving portions.

Figure 1B:
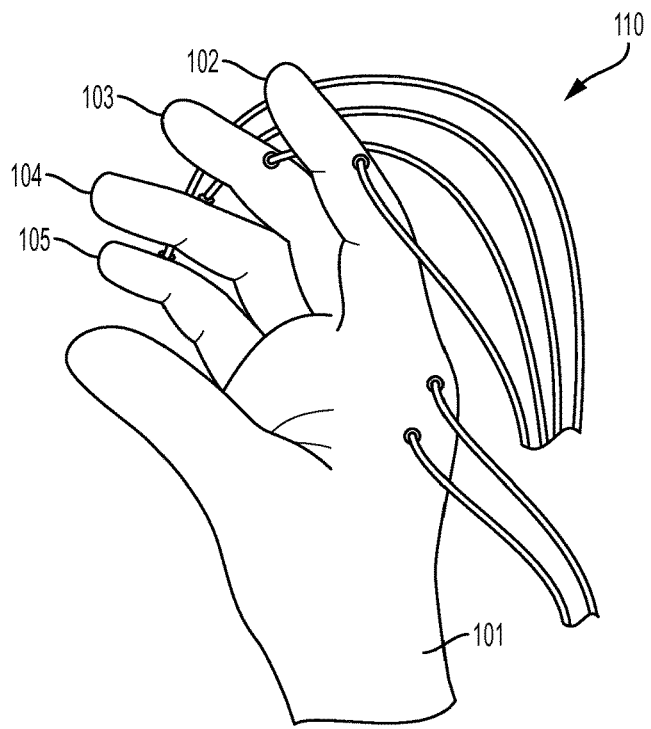

FIG. 1B illustrates an embodiment of a sealable enclosure 101 in a flexed position 110. As illustrated, each digit receiving portion 102, 103, 104, and 105 is positioned at variable degrees relative to sealable enclosure 101 and relative to the other individually articulable digit receiving portions.

FIGS. 1A-1B illustrate an embodiment of the invention with each individually articulable digit receiving portion configured to move independently relative to sealable enclosure 101 and the other individually articulable digit receiving portions; however, one having skill in the art can envision embodiments that employ splints or other mechanisms to prevent independent motion of any one or more individually articulable digit receiving portion relative to sealable enclosure 101 or the other individually articulable digit receiving portions. For example, a splint mechanism (not shown) may couple first individually articulable digit receiving portion 102 and second individually articulable digit receiving portion 103 such that their movement is configured to move identically with one another, while third individually articulable digit receiving portion 104 is configured to move independently.

Figure 2A:
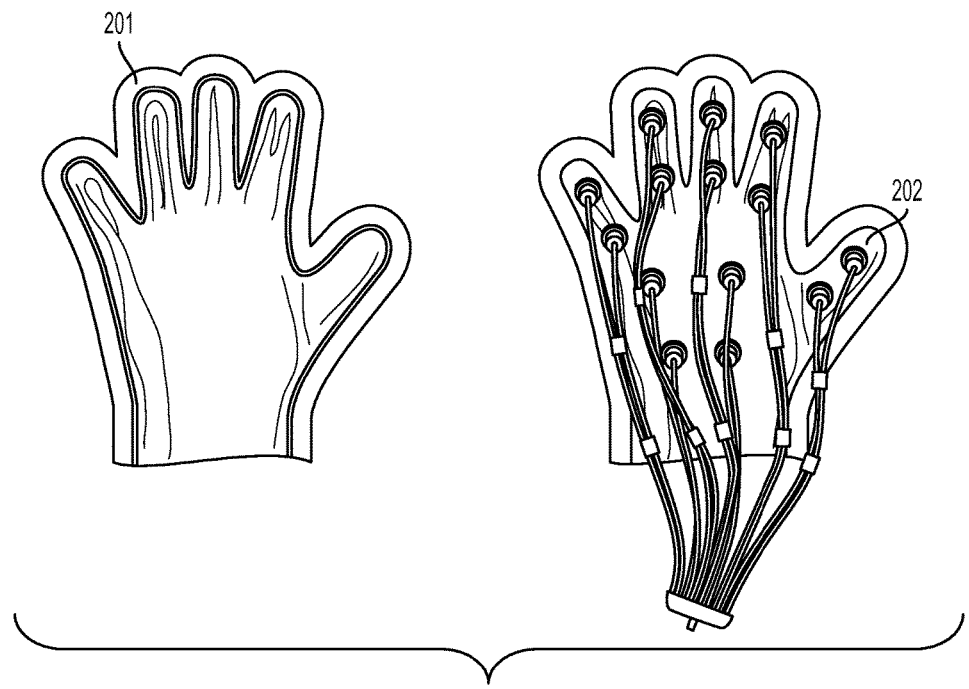
FIGS. 2A-2B illustrate layers of a partially translucent sealable enclosure of a device enclosing a hand according to an embodiment of the present invention.
Figure 2B:
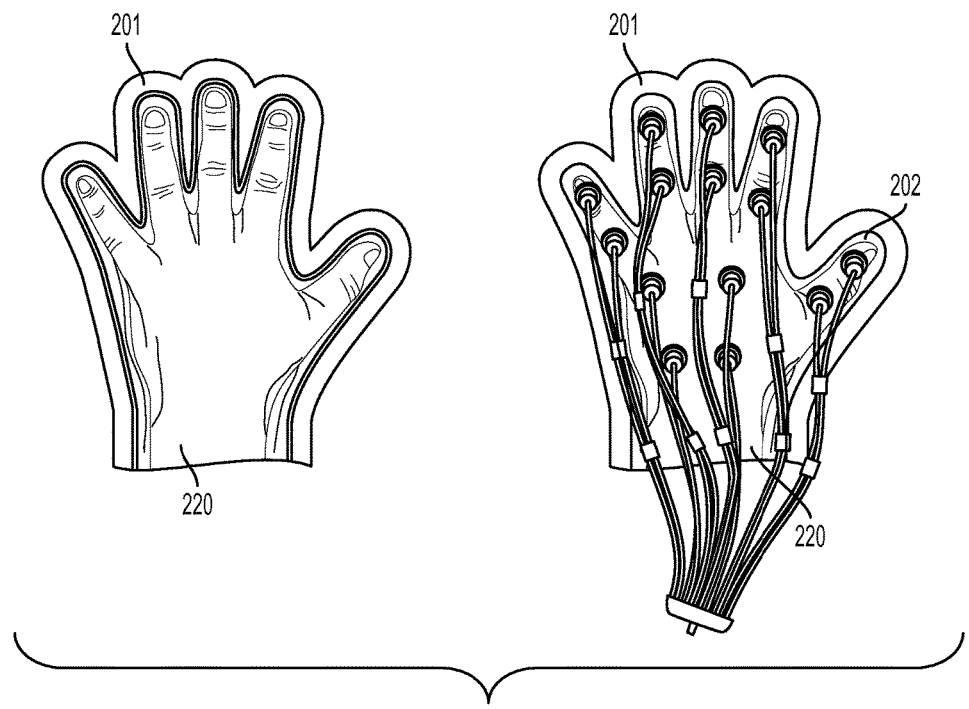

As illustrated in FIG. 2A, an exemplary embodiment comprises a sealable enclosure with a first layer 201 made from an at least partially translucent material and a second layer 202 made from an at least partially translucent material. As illustrated in FIG. 2B, the outline of first layer 201 is complementary to the outline of second layer 202 such that when extremity 220 is placed in first layer 201, and second layer 202 is coupled to first layer 201 the outlines of the two layers align for sealing to create a fluid tight interface. Further illustrated in FIG. 2B is the capability to visually inspect extremity 220 when enclosed between first layer 201 and second layer 202. The visual inspection of extremity 220 is enabled by the at least partially translucent material of first layer 201 or second layer 202. Other materials suitable for visual inspection are of course possible, and in one embodiment the at least partially translucent material is transparent.

Figure 3A:
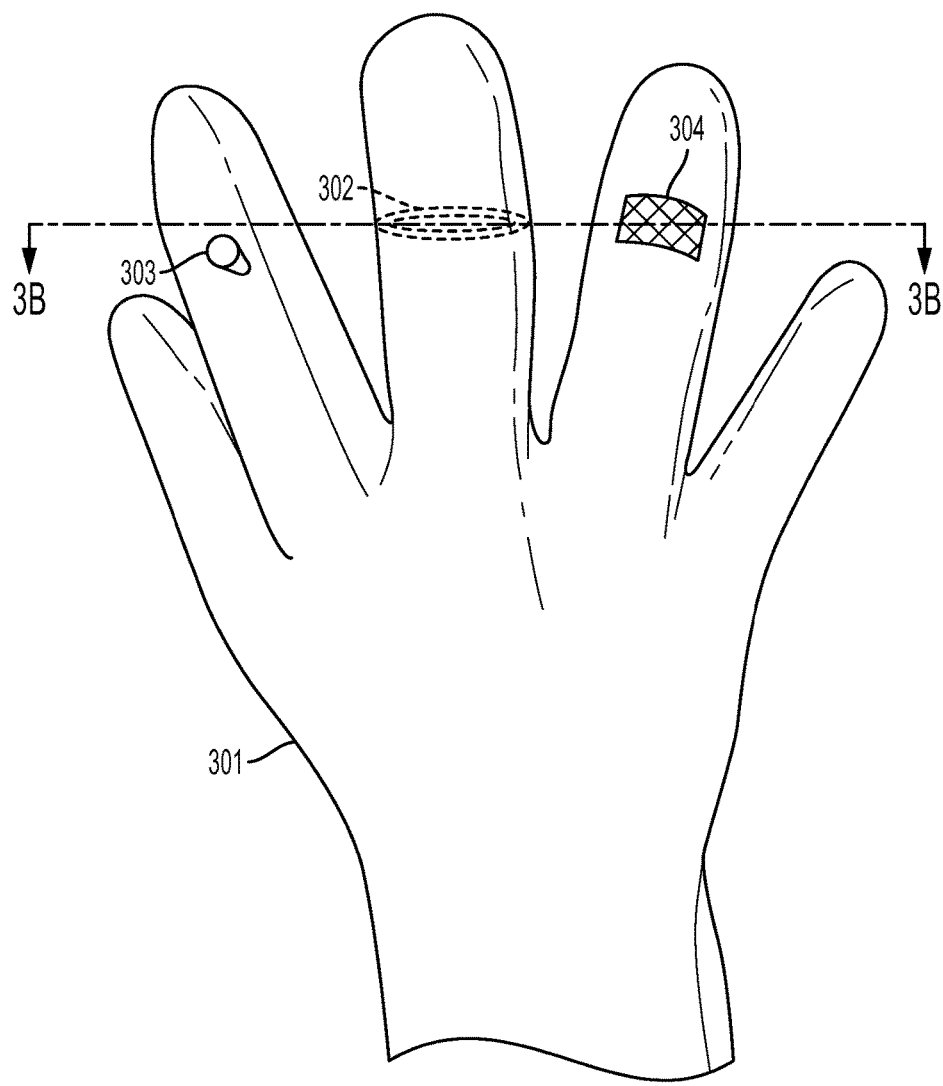
FIGS. 3A-3B illustrate a sealable enclosure with a hoop scaffold fixture, support member scaffold fixture, and an outer surface scaffold fixture according to embodiments of the present invention.

As illustrated in FIG. 3A, sealable enclosure 301 includes scaffold structures according to various embodiments. In one embodiment, a hoop 302 in a digit receiving portion lines the inner surface of the sealable enclosure 301. Similarly, in other embodiments support member 303 lines the inner surface of a digit receiving portion of sealable enclosure 301. Hoop 301 and support member 303 create a mechanical scaffold coupled to the inner surface of sealable enclosure 301 such that sealable enclosure 301 is propped up when sealed around an injury and contact between the injury and sealable enclosure 301 is precluded.

The specific height, width, and placement of hoop 302 or support member 303 varies according to embodiments to preclude contact between the injury and sealable enclosure 301 for various locations of injuries that may be sealed within. In other embodiments, a plurality of hoop 302 or a plurality of support member 303 lines the inner surface of sealable enclosure 301. It not necessary for FIG. 3A to illustrate all possible numbers, orientations, and arrangements of hoop 302 and support member 303 for one having skill in the art to appreciate variations and modifications possible from the illustration provided. One having skill in the art will further recognize that while FIG. 3A illustrates a sealable enclosure for a hand, other extremities are of course possible and hoop 302 and support member 303 are not limited to digit receiving portions but rather lines the inner surface of the appropriate portion of sealable enclosure 301 to preclude contact with an injury the sealable enclosure 301 is enclosed around.

Further illustrated in FIG. 3A is outer surface fixture 304 coupled to the outer surface of sealable enclosure 301. Outer surface fixture 304 is made from a material with a higher rigidity than the material of sealable enclosure 301, such that its tensile modulus is at least greater than that of sealable enclosure 301 and outer surface fixture 304 pulls sealable enclosure 301 away from the outer surface of an enclosed extremity and any injury on an enclosed extremity. The higher rigidity of the outer surface fixture 304 precludes the sealable enclosure from collapsing inward towards the outer surface of the extremity while static or in motion.

Similar to hoop 302 or support member 303, the specific height, width, length, and placement of outer surface fixture 304 varies according to embodiments to preclude contact between the injury and sealable enclosure 301 for various locations of injuries that may be sealed within. In other embodiments, a plurality of outer surface fixture 304 lines the inner surface of sealable enclosure 301. It not necessary for FIG. 3A to illustrate all possible numbers, orientations, and arrangements of outer surface fixture 304 for one having skill in the art to appreciate variations and modifications possible from the illustration provided.

Figure 3B:
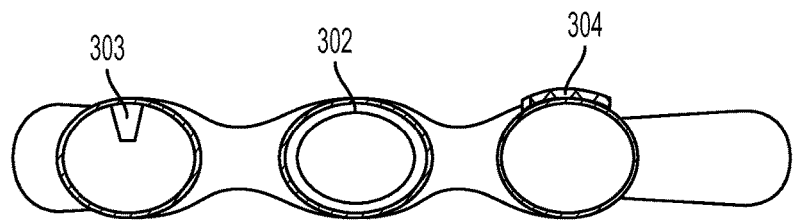

FIG. 3B is a cross sectional view of sealable enclosure 301, illustrating the inner lining of hoop 302, the inner placement of support member 303, and external placement of outer surface fixture 304. One having skill in the art will further recognize that while FIGS. 3A-3B illustrate a sealable enclosure for a hand, other extremities are of course possible and outer surface fixture 304 is not limited to the back of the hand, but rather is affixed to the appropriate portion of sealable enclosure 301 to preclude contact with an injury the sealable enclosure 301 is enclosed around.

Figure 4:
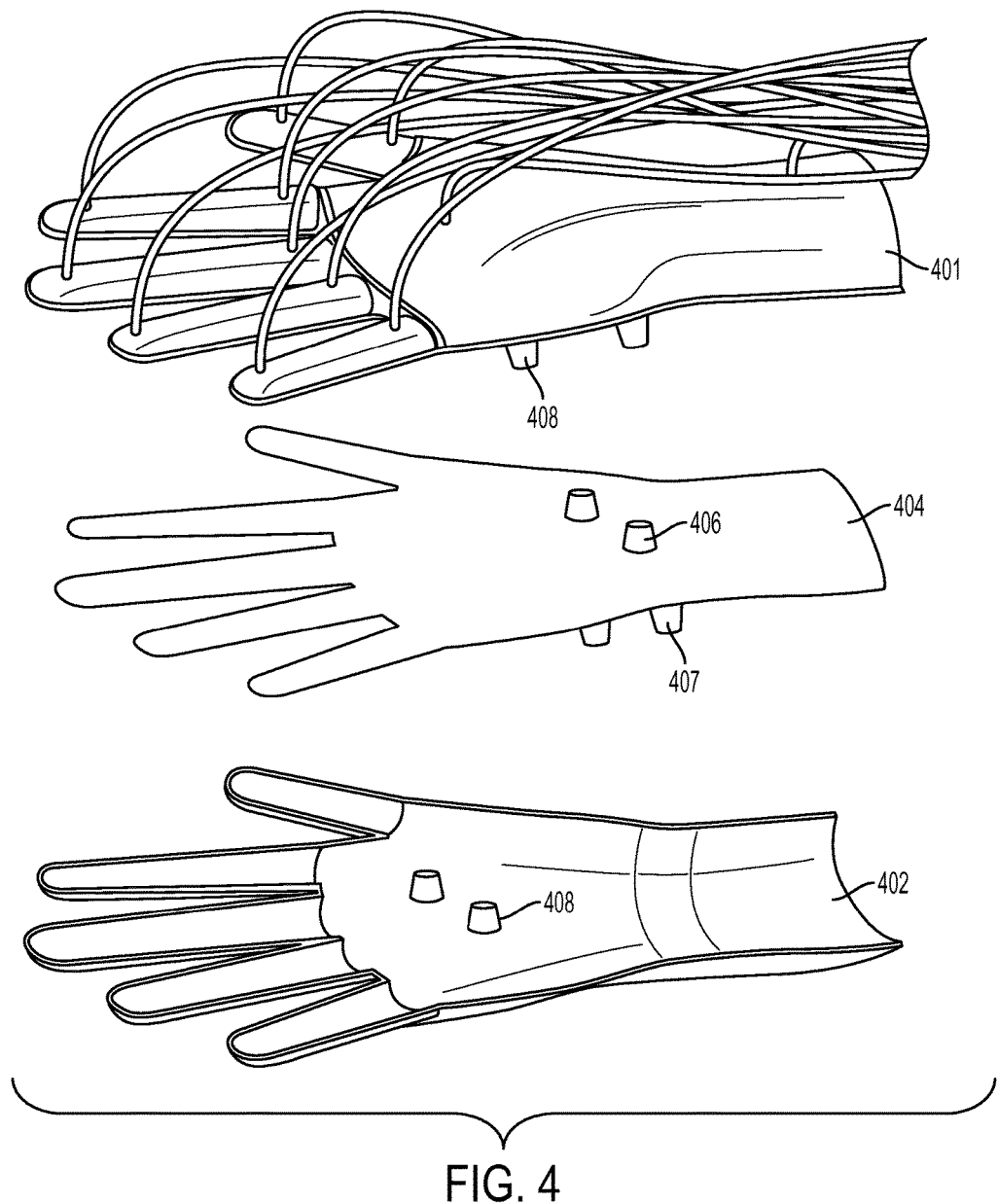
FIG. 4 illustrates a membrane scaffold structure and pillars, the membrane scaffold situated between a first layer and a second layer of a sealable enclosure according to embodiments of the present invention.

FIG. 4 illustrates an embodiment with a scaffold structure as membrane 404. Membrane 404 is situated between a first sealable enclosure layer 401 and a second sealable enclosure layer 402. According to one embodiment, membrane 404 further includes first pillars 406 extending from membrane 404 towards the inner surfaces of first sealable enclosure layer 401 or second sealable enclosure layer 402. First pillars 406 separate contact between the inner surfaces of first sealable enclosure layer 401 or second sealable enclosure layer 402 and membrane 404. This separation of contact creates a fluid flow cavity layer between membrane 404 and first sealable enclosure layer 401 or second sealable enclosure layer 402. The fluid flow cavity layer facilitates removal of fluids or other exudates, the application of materials, and the preclusion of suction seal against first sealable enclosure layer 401 or second sealable enclosure layer 402.

In other embodiments, membrane 404 includes second pillars 407. Second pillars 407 extend from membrane 404 away from the inner surfaces of first sealable enclosure layer 401 or second sealable enclosure layer 402 to separate contact between the membrane and an enclosed extremity. This separation of contact creates a fluid interface cavity layer between membrane 404 and an enclosed extremity. The fluid interface cavity layer maintains fluid contact with an injury to an enclosed extremity.

In still other embodiments, surface pillars 408 coupled to the inner surfaces of first sealable enclosure layer 401 or second sealable enclosure layer 402 extend towards membrane 404. Surface pillars 408 create a fluid flow cavity layer between membrane 404 and first sealable enclosure layer 401 or second sealable enclosure layer 402. The description for a fluid flow cavity layer formed by first pillars 406 is the same for surface pillars 408.

Figure 5:
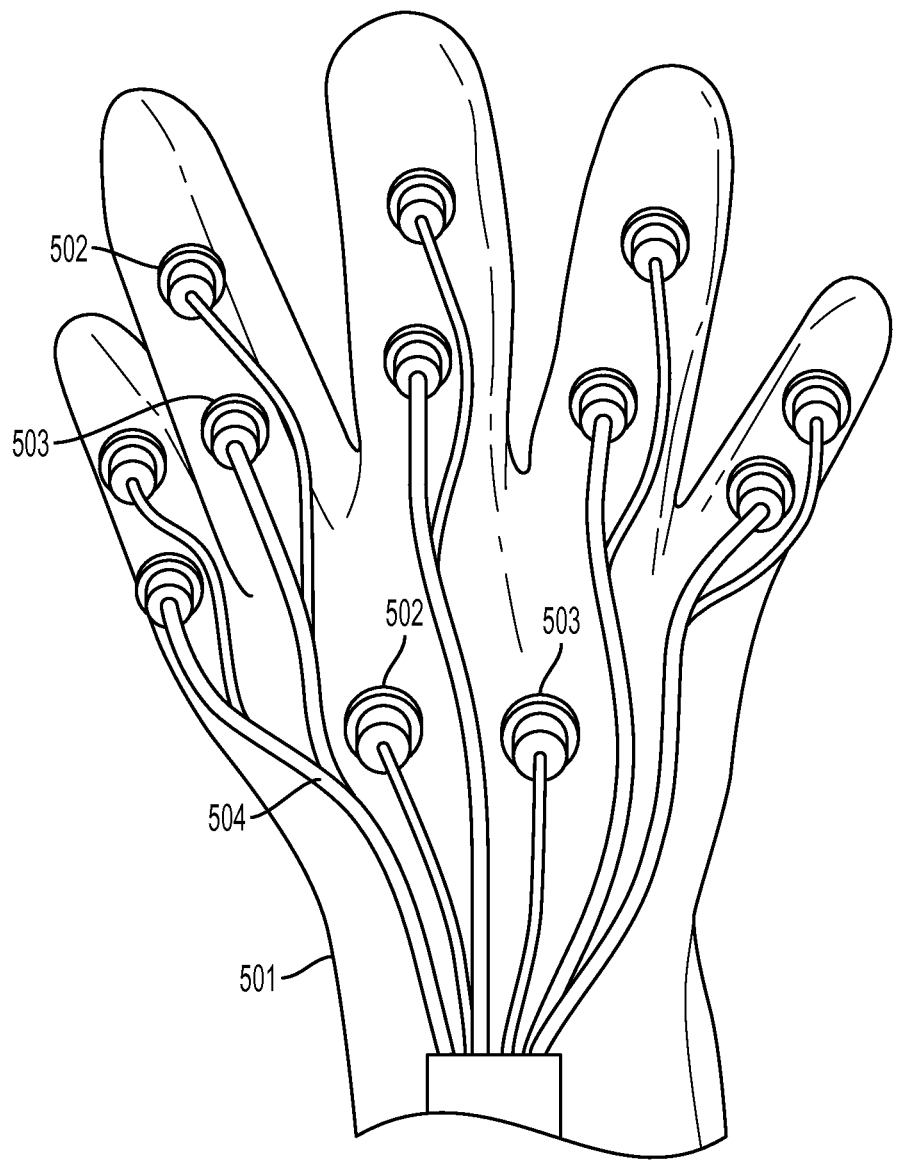
FIG. 5 illustrates a plurality of individually addressable ports coupled to a sealable enclosure according to an embodiment of the present invention.

FIG. 5 illustrates a plurality of individually addressable ports coupled to sealable enclosure 501 according to an embodiment. Suction port 502 extracts a medium from within sealable enclosure 501. Delivery port 503 delivers a material to the interior of sealable enclosure 501. Delivery lines 504 facilitate transport of a medium away from sealable enclosure 501 via suction port 502, or transport of a material to sealable enclosure via delivery port 503. The location and number of the plurality of individually addressable ports varies in accordance with embodiments of the invention.

Figure 6:
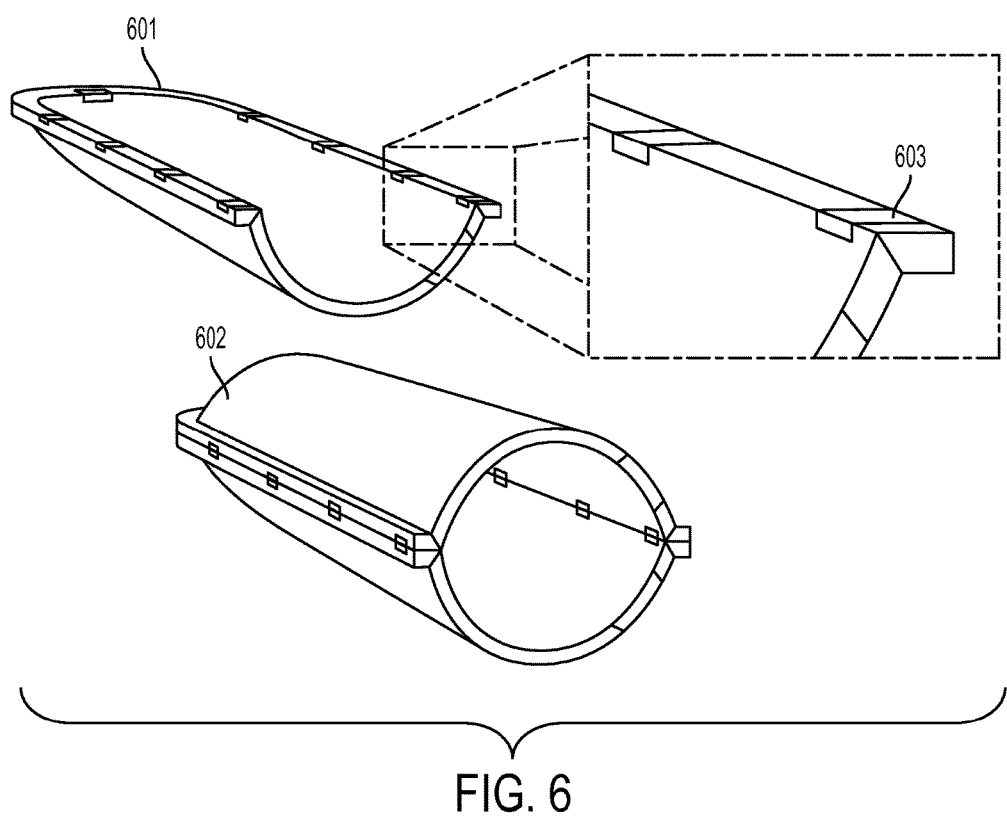
FIG. 6 illustrates a layer of a digit receiving portion, a magnified view of a sealing interface on a first layer of a sealable enclosure of the digit receiving portion, and a complementary layer sealed with the first layer according to an embodiment of the present invention.

FIG. 6. illustrates a first layer 601 of a digit receiving portion and a second layer 602 of a digit receiving portion. First layer 601 includes a sealing interface 603 along a portion of the periphery of the rim of first layer 602. Second layer 602 includes a similar sealing interface 603 along the rim of its periphery. When the respective sealing interface 603 of first layer 601 and second layer 602 align it creates a fluid tight seal. FIG. 6 illustrates sealing interface 603 as a magnetic seal, though one having skill in the art would envision alternative sealing interface 603 according to other embodiments of the invention such as adhesives, or an interlocking groove on one layer and a locking ridge on the other layer (for example, Ziploc®) interfaces.

Figure 7:
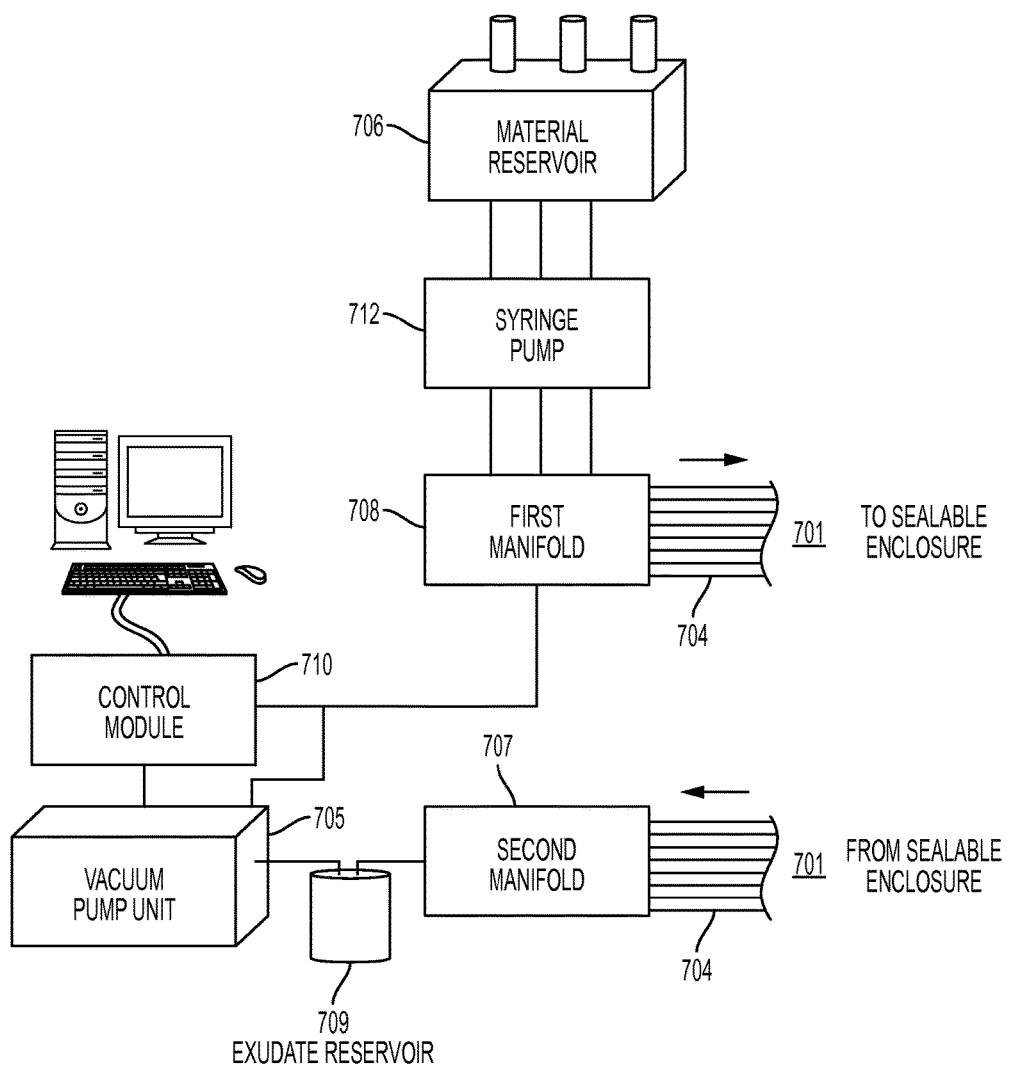
FIG. 7 is a block diagram of a vacuum pump and manifold system coupled to delivery lines and a sealable enclosure, reservoirs for materials, exudate reservoirs, and a control module according to an embodiment of the present invention.

As illustrated in FIG. 7, embodiments of the invention include a vacuum pump unit 705 coupled to at least one material reservoir 706. Vacuum pump unit 705 pumps material from at least one material reservoir 706 to sealable enclosure 701 via delivery lines 704 and first manifold 708. In one embodiment, at least one syringe pump 712 pumps material from material reservoir 706 to first manifold 708. Other embodiments comprise exudate reservoir 709; vacuum pump unit 705 extracts at least one medium from sealable enclosure 701, and in one embodiment transports the extracted medium to exudate reservoir 709 via delivery lines 704 and second manifold 707. In one embodiment, control module 710 operates vacuum pump unit 705. Control module 710 operations include the frequency of operation of vacuum pump unit 705 (for example, continuous operation or selective operation), as well as which material to deliver from material reservoir 706.

In embodiments with a plurality of delivery ports, control module 710 further commands which delivery port coupled to sealable enclosure 701 will deliver material from material reservoir 706 and which delivery line 704 to transport material to the sealable enclosure via the selected delivery port. In other embodiments with a plurality of suction ports, control module 710 further commands which suction port coupled to sealable enclosure 701 will extract a medium from sealable enclosure 701, if the medium is to be transported to exudate reservoir 708 and which delivery line 704 will transport the extracted medium to exudate reservoir 708.

Figure 8A:
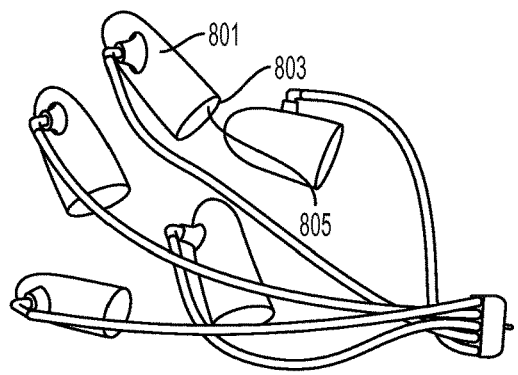
FIGS. 8A-8C illustrate a single structure digit receiving portion and a single structure extremity housing portion, each having receiving apertures and sealing interfaces on the rim of the receiving apertures, and a sealed enclosure combining the single structure digit receiving portion and extremity housing portion according to embodiments of the present invention.
Figure 8B:
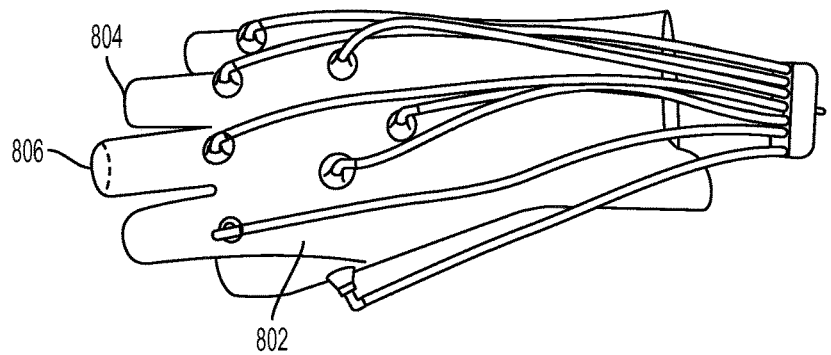

As illustrated in FIG. 8A, digit receiving portion 801 is a single structure with a digit sealing interface 803 on the rim of a digit receiving aperture 805. Digit sealing interface 803 binds to an anchor to create a fluid tight seal for an enclosed digit. As illustrated in FIG. 8B is extremity housing portion 802 with extremity sealing interface 804 on extremity receiving aperture 806. Sealing interface 804 binds to an anchor to create a fluid tight seal for an enclosed extremity. Anchors for sealing are previously discussed in this disclosure.

Figure 8C:
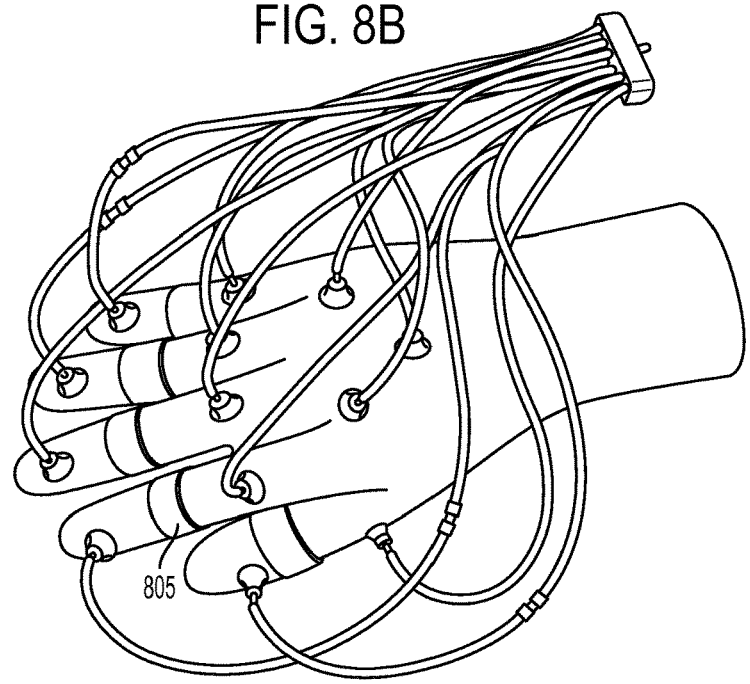

In one embodiment illustrated in FIG. 8C, sealing interface 803 joins sealing interface 804 at 805; that is, the digit receiving aperture 805 and extremity receiving aperture 806 also align. At 805, the extremity housing portion 802 is an anchor for digit receiving portion 801; similarly, digit receiving portion 801 is an anchor for extremity housing portion 802. The description of the various ways to seal is previously discussed in this disclosure, for example the sealing interface 503 of FIG. 5 is applicable to digit sealing interface 803 and extremity sealing interface 804. In one embodiment, only digit receiving portion 801 is utilized and digit sealing interface 803 is applied to an enclosed digit to serve as an anchor. In another embodiment, only extremity housing portion 802 is employed, (e.g. a fingerless glove) and extremity sealing interface 804 is applied to an enclosed extremity to serve as an anchor. One having skill in the art can envision embodiments employing multiple digit receiving portions 801 in conjunction with an extremity housing portion 802, embodiments employing only digit receiving portions 801, or embodiments employing only an extremity housing portion 802.

Figure 9:
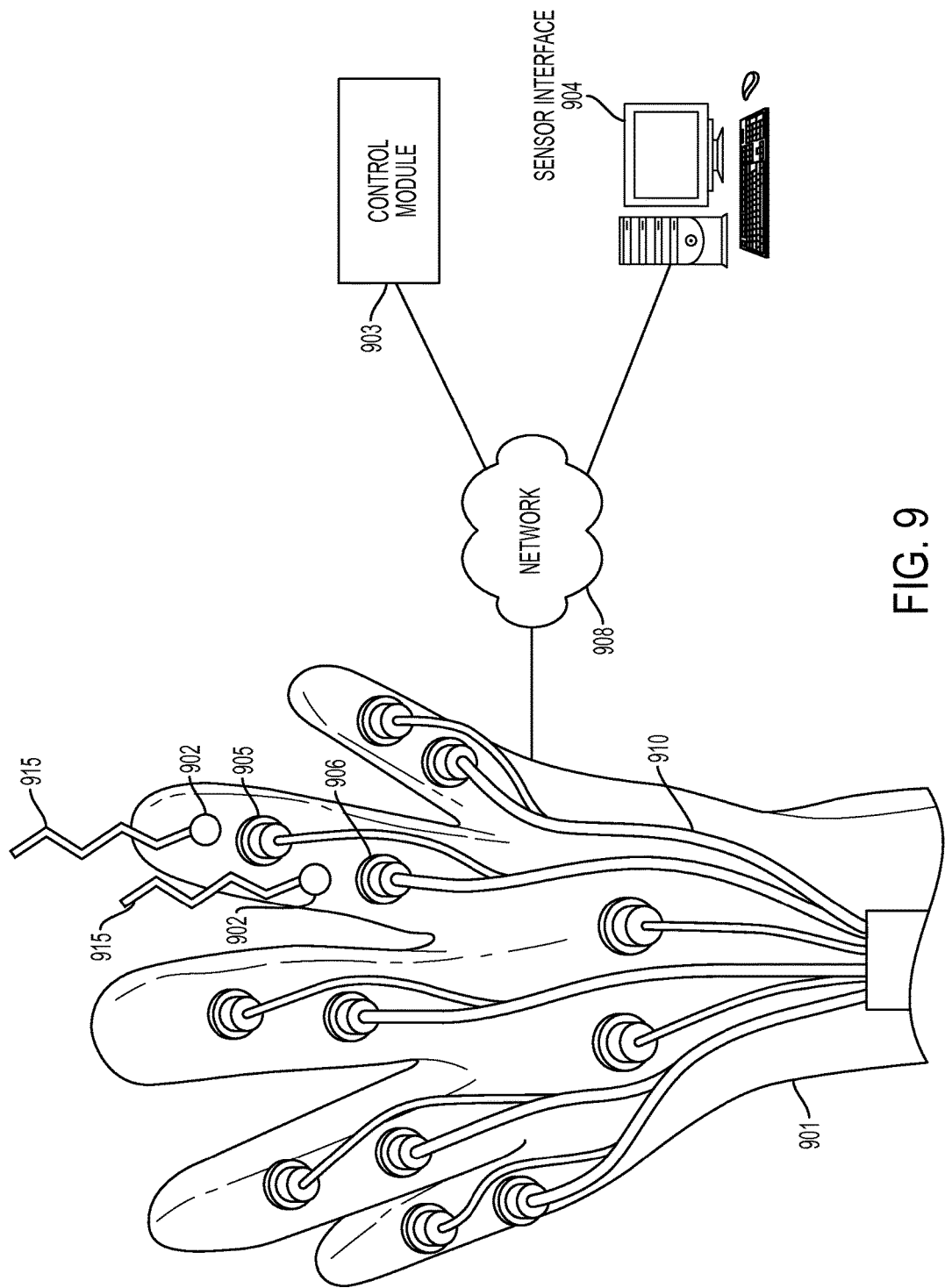
FIG. 9. illustrates a plurality of sensors coupled to a sealable enclosure, a sensor interface to record and display sensor information, and a control module to respond to sensor information according to an embodiment of the present invention.

As illustrated in FIG. 9, sealable enclosure 901 is coupled to a plurality of sensors 902. Sensors 902 may detect conditions of the sealable enclosure, including internal conditions such as temperature, pH levels, and oxygen tension. In another embodiment, sensors 902 further measure performance of the delivery ports 905 or the suction ports 906. In other embodiments, sensors 902 are coupled to delivery line 910 and measure conditions of material delivered or medium extracted, such as pH levels in exudate or biologic levels of the extracted medium such as cytokines or bacteria. A control module 903 may receive data detected by sensors 902. In one embodiment, control module 903 further displays collected data on sensor interface 904. In another embodiment, control module 903 adjusts the properties of materials delivered by the plurality of delivery ports 905 or mediums extracted by the plurality of suction ports 906 in response to the data detected by sensors 902. For example, if sensors 902 detect ambient pressure in sealable enclosure 902, control module 903 increases extraction of medium through the plurality of suction ports 906 to restore a negative pressure environment. One having skill in the art will envision other responses of control module 903 to administer certain environments to sealable enclosure 901.

In one embodiment, control module 903 receives data detected by sensors 902 through wired connections 915. In an alternative embodiment, control module 903 receives data detected by sensors 902 through network 908. Network 908 may be wireless internet, cellular network, or other suitable network. Sensor interface 904 may also receive detected datum from sensors 902 through wired connections 915 or network 908. Sensor interface 904 in one embodiment, as illustrated in FIG. 9, is a desktop computer. Sensor interface 904 in another embodiment is a mobile phone or other mobile device such as a tablet computer.

While the invention has been described in terms of particular embodiments and illustrative figures, those of ordinary skill in the art will recognize that the invention is not limited to the embodiments or figures described. For example, in various embodiments described above, a vacuum pump unit enables delivery of a material into a sealable enclosure by creating a suction and pulling the material through a series of delivery lines. However, in other embodiments, material is delivered from the material reservoir by a pump that pushes the material through a series of delivery lines. As another example, in various embodiments described above, a manifold system separates material delivered from a material reservoir for assignment to multiple individually addressable delivery ports or combines medium received from multiple individually addressable suction ports to a common line feeding an exudate reservoir. However, in other embodiments, no manifold system is present and the respective material reservoirs and exudate reservoirs connect directly to a single delivery port or suction port respectively. As another example, in various embodiments discussed above, negative pressure is applied to the sealable enclosure. However, in another embodiment, fluid delivery of antibiotics is delivered. In still other embodiments, both negative pressure and fluid delivery are applied to the sealable enclosure.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one," "at least one" or "one or more." Unless otherwise required by context, singular terms used herein shall include pluralities and plural terms shall include the singular.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While specific embodiments and examples for the disclosure are described herein for illustrative purposes, various equivalent modifications are possible within the scope of the disclosure, as those skilled in the relevant art will recognize. Such modifications may include, but are not limited to, changes in the dimensions and/or the materials shown in the disclosed embodiments.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

What is claimed is:

1. A medical device, comprising:
a sealable enclosure having an inner surface configured to enclose at least a portion of an extremity having an outer surface, wherein the sealable enclosure is flexible and at least partially translucent;
a scaffold structure coupled to the sealable enclosure configured to separate at least a portion of the inner surface of the sealable enclosure from the outer surface of the extremity,
wherein the scaffold structure comprises a porous membrane coupled to the inner surface of the sealable enclosure, wherein the porous membrane comprises pillars configured to be situated between an inner surface of the porous membrane and the outer surface of the extremity, thereby creating a fluid flow cavity layer; and
a plurality of individually addressable ports provided in the sealable enclosure for controlling an environment within the sealable enclosure,
wherein the sealable enclosure comprises a plurality of digit receiving portions, each digit receiving portion configured to move relative to other digit receiving portions.

2. The medical device of claim 1, wherein the plurality of individually addressable ports comprises:
at least one suction port for extracting at least one medium from the sealable enclosure; and
at least one delivery port for delivering a material to the outer surface of the extremity.

3. The medical device of claim 2, further comprising a vacuum pump unit coupled to the plurality of individually addressable ports for manipulating the environment within the sealable enclosure.

4. The medical device of claim 3, wherein the vacuum pump unit maintains an aqueous environment within the sealable enclosure by adjusting a mass flow rate of the material relative to a mass flow rate of the at least one medium.

5. The medical device of claim 3, further comprising:
a reservoir for storing the material; and
a first manifold coupled to the at least one delivery port and the reservoir for transporting the material from the reservoir to at least one delivery port.

6. The medical device of claim 5, further comprising a control module for adjusting at least one input property of the material.

7. The medical device of claim 5, further comprising a second manifold coupled to the at least one suction port for transporting the at least one medium extracted from the sealable enclosure.

8. The medical device of claim 1, wherein the sealable enclosure is transparent.

9. The medical device of claim 1, wherein the sealable enclosure comprises silicone.

10. The medical device of claim 2, wherein the material comprises one or more of cytokines, growth factors, and stem cells.

11. The medical device of claim 6, wherein the at least one input property of the material comprises one or more of temperature, time of delivery, and location of delivery port.

12. The medical device of claim 1, wherein the scaffold structure comprises at least one fixture having a tensile modulus greater than the sealable enclosure coupled to the sealable enclosure.

13. The medical device of claim 1, further comprising a therapeutic agent coupled to the porous membrane.

14. The medical device of claim 1, wherein the scaffold structure further comprises a plurality of support members coupling the porous membrane to the inner surface of the sealable enclosure to define, at least in part, the fluid flow cavity layer between the porous membrane and the inner surface of the sealable enclosure.

15. The medical device of claim 1, further comprising:
a plurality of sensors configured to detect at least one biological datum within the sealable enclosure.

16. The medical device of claim 15, further comprising:
a sensor interface coupled to the plurality of sensors configured to display the at least one biological datum detected by the plurality of sensors.

17. The medical device of claim 6, further comprising:
a plurality of sensors detecting at least one biological datum within the sealable enclosure;
wherein the control module adjusts the input property of the material in response to the at least one biological datum detected by the plurality of sensors.

18. The medical device of claim 3, wherein:
the sealable enclosure comprises an extremity housing portion coupled to five digit receiving portions, the extremity housing portion being configured to receive a palm of the extremity and each of the five digit receiving portions is configured to receive a digit of the extremity.

19. The medical device of claim 1, wherein the sealable enclosure further comprises:
a first extremity receiving layer having a first peripheral sealing interface; and
a second extremity receiving layer having a second peripheral sealing interface,
wherein the first peripheral sealing interface is coupled to the second peripheral sealing interface to define an enclosed cavity for the received extremity.

20. The medical device of claim 19, wherein:
the first extremity receiving layer comprises an extremity housing portion coupled to five digit receiving portions and is configured to be positioned on a front side of the received extremity; and
the second extremity receiving layer comprises an extremity housing portion coupled to five digit receiving portions and is configured to be positioned on a back side of the received extremity.

* * * * *